United States Patent [19]

Kubota et al.

[11] Patent Number: 4,989,588
[45] Date of Patent: Feb. 5, 1991

[54] MEDICAL TREATMENT DEVICE UTILIZING ULTRASONIC WAVE

[75] Inventors: Tetsumaru Kubota; Akira Shiga; Akio Nakada; Syuichi Takayama; Ryouichi Konou; Yasuhiro Ueda; Hitoshi Karasawa; Tatsuo Nagasaki; Koji Taguchi; Hiroyoshi Fujimori; Shinichi Imade; Shinji Hatta; Yutaka Ohshima; Hiroyuki Kusunoki; Toshiki Terayama; Masaaki Hayashi; Tadao Hagino; Akihiro Taguchi, all of Tokyo, Japan

[73] Assignee: Olympus Optical Co., Ltd., Tokyo, Japan

[21] Appl. No.: 20,333

[22] Filed: Feb. 27, 1987

[30] Foreign Application Priority Data

| Mar. 10, 1986 | [JP] | Japan | 61-51668 |
| Mar. 13, 1986 | [JP] | Japan | 61-55511 |
| Mar. 14, 1986 | [JP] | Japan | 61-56416 |
| Mar. 17, 1986 | [JP] | Japan | 61-58602 |
| Mar. 18, 1986 | [JP] | Japan | 61-59878 |
| Jun. 11, 1986 | [JP] | Japan | 61-135179 |
| Jun. 12, 1986 | [JP] | Japan | 61-136846 |

[51] Int. Cl.$^5$ ............................................. A61B 17/20
[52] U.S. Cl. ..................................... 128/24 A; 604/22
[58] Field of Search ............... 128/24 A, 305; 604/22, 604/43

[56] References Cited

U.S. PATENT DOCUMENTS

| 3,584,327 | 4/1969 | Murry | 128/24 A |
| 3,861,391 | 1/1975 | Antonevich et al. | 128/24 AA |
| 3,990,452 | 11/1976 | Murry et al. | 128/24 A |
| 4,535,771 | 8/1985 | Takayama | 128/328 |
| 4,587,958 | 5/1986 | Noguchi et al. | 128/24 A |
| 4,708,127 | 11/1987 | Abdelghani | 128/24 AA |
| 4,750,902 | 6/1988 | Wuchinich et al. | 128/24 AA X |

FOREIGN PATENT DOCUMENTS 61-159953  7/1986  Japan ............................. 128/24 A Primary Examiner—Francis Jaworski
Attorney, Agent, or Firm—Frishauf, Holtz, Goodman & Woodward

[57] ABSTRACT

A medical treatment device for resecting, e.g., a prostate or breaking a bladder stone, which includes a vibrator for generating ultrasonic vibrations, a horn connected to the vibrator, a casing for accommodating the vibrator and the horn, a probe connected to the front portion of the horn to transmit ultrasonic vibrations generated by the vibrator, and a power source unit for supplying a drive voltage to the vibrator, the power source unit having an oscillator for producing a wave having a frequency for vibrating the probe and a frequency switching circuit for selecting an oscillating frequency at which the distal end of the probe serves as a loop of vibration or a frequency at which the distal end of the probe serves as a node of vibration.

13 Claims, 14 Drawing Sheets

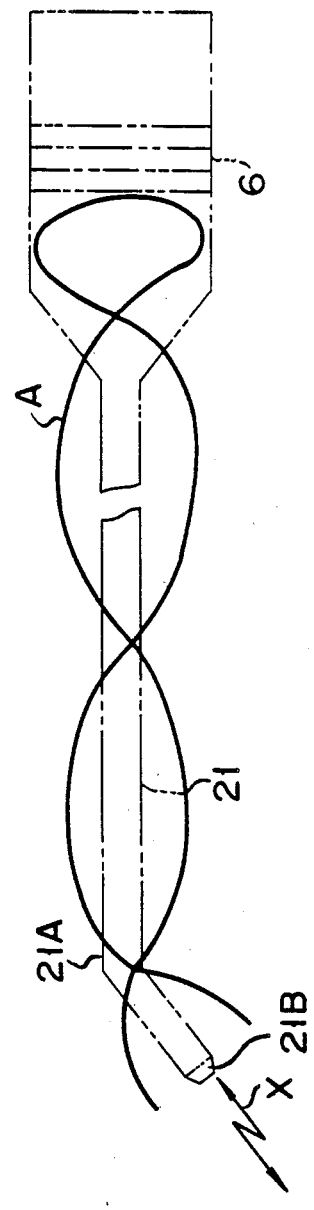
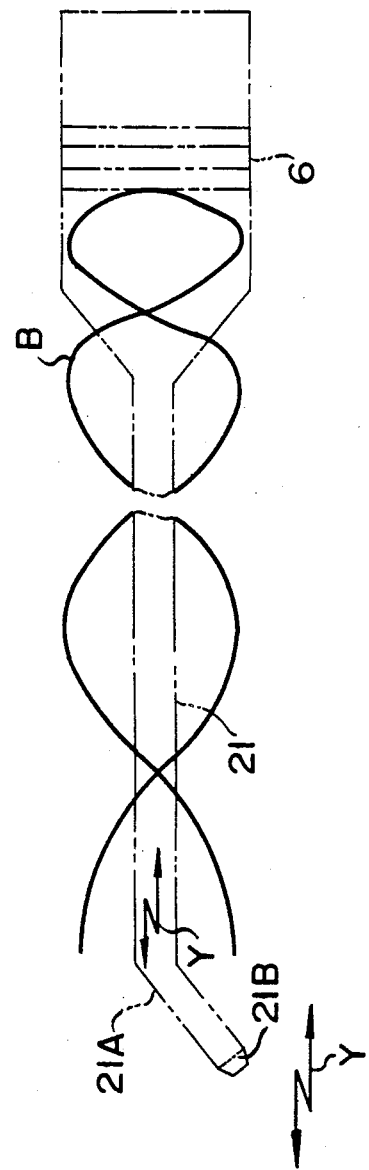

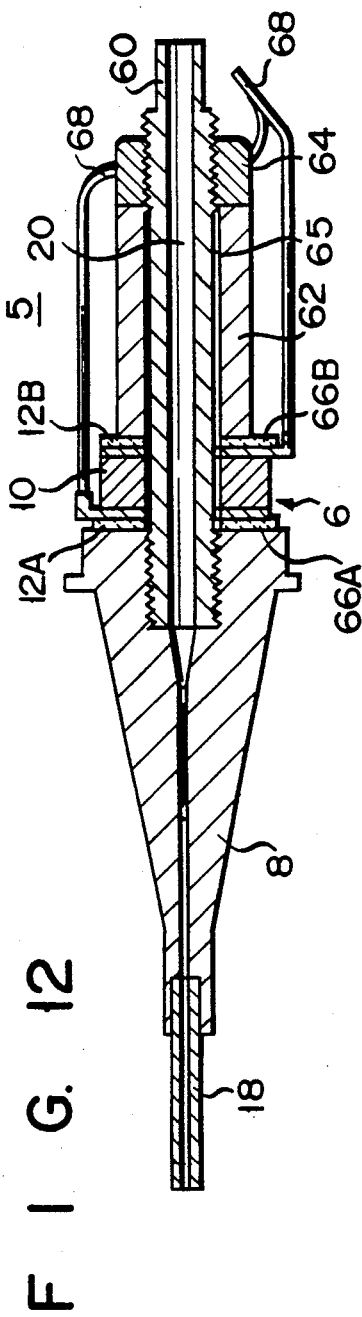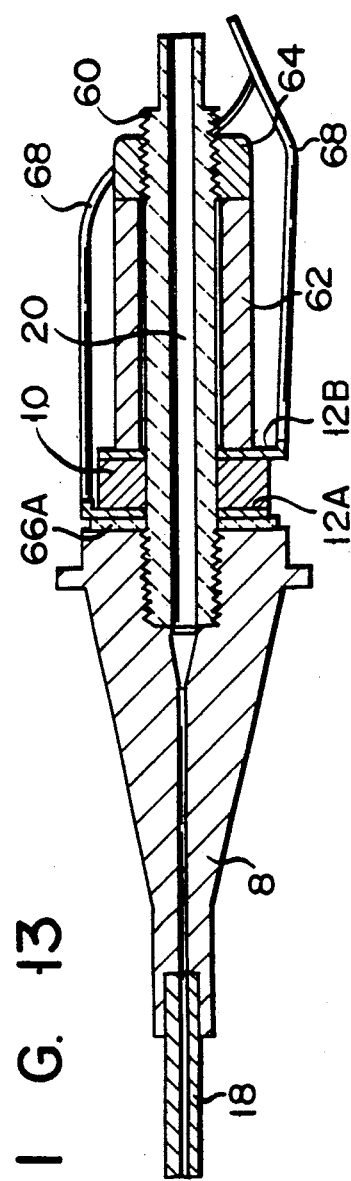

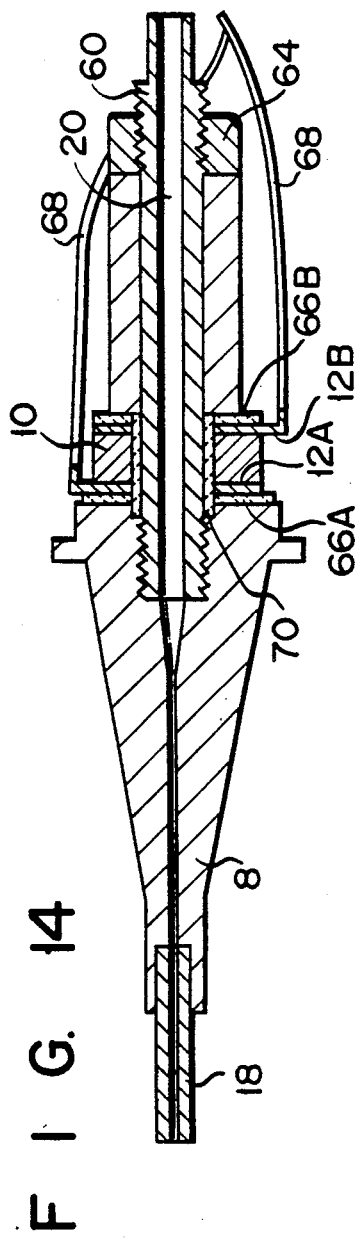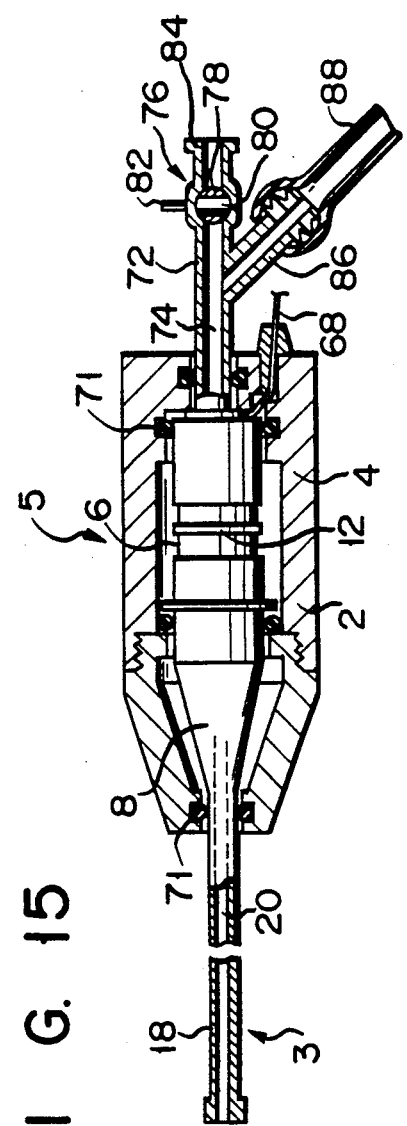
FIG. 14
FIG. 15

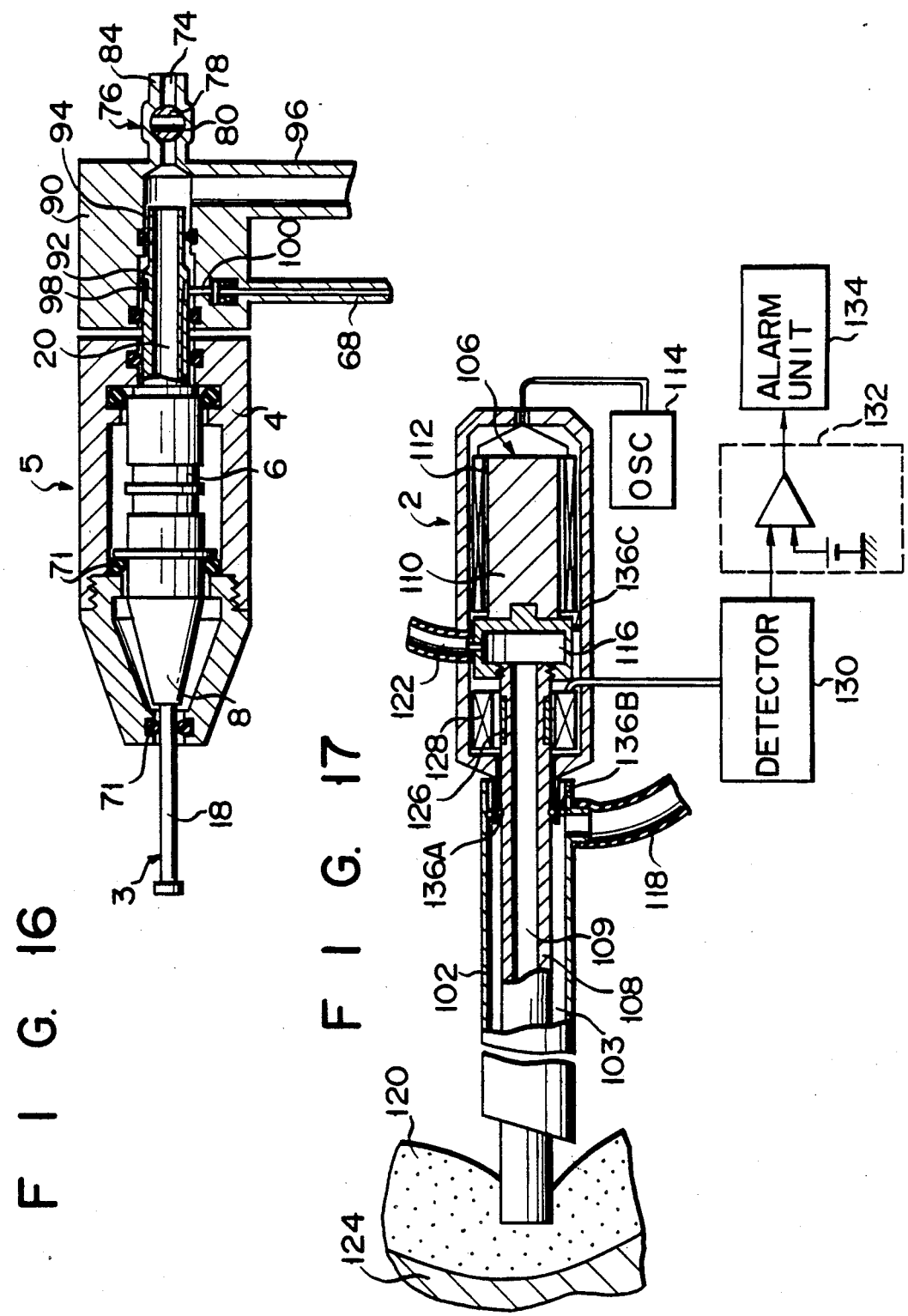

F I G. 21
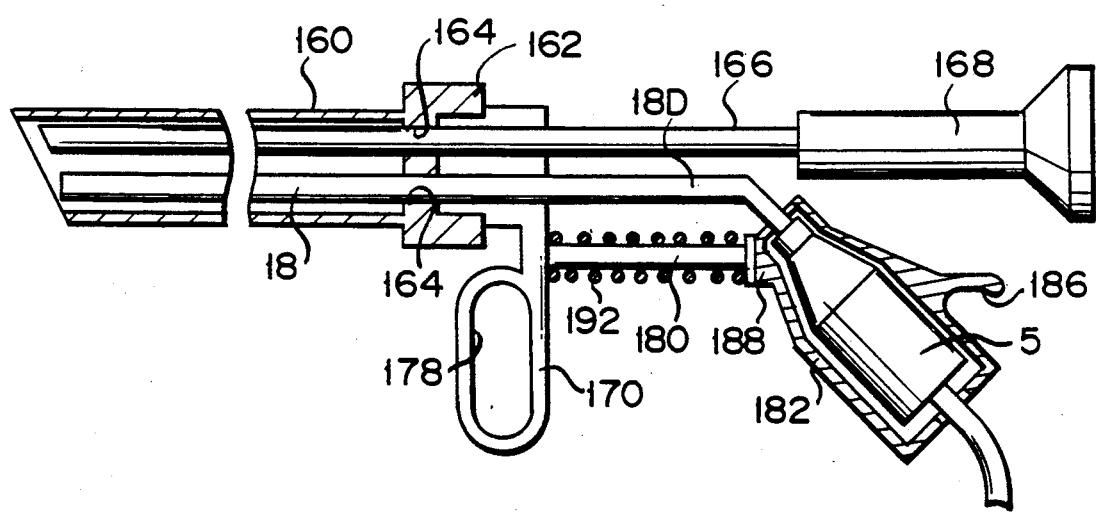
F I G. 22
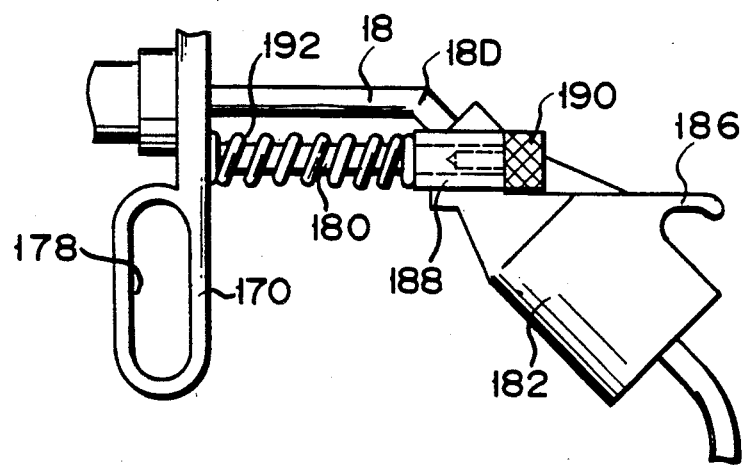

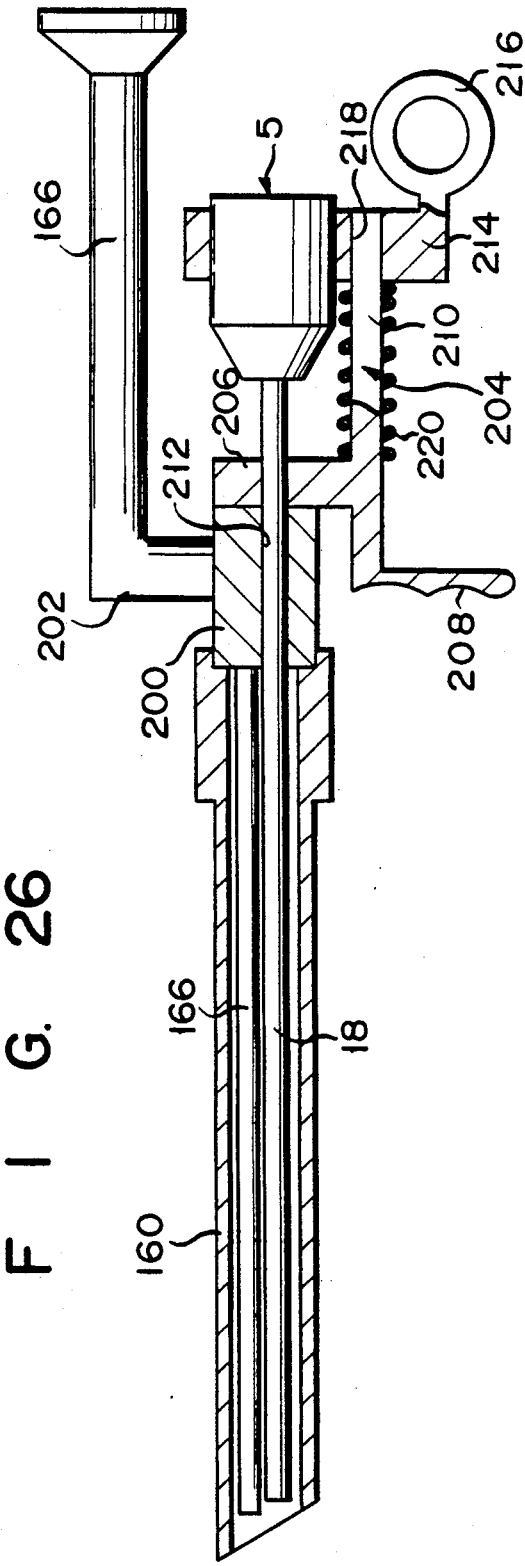
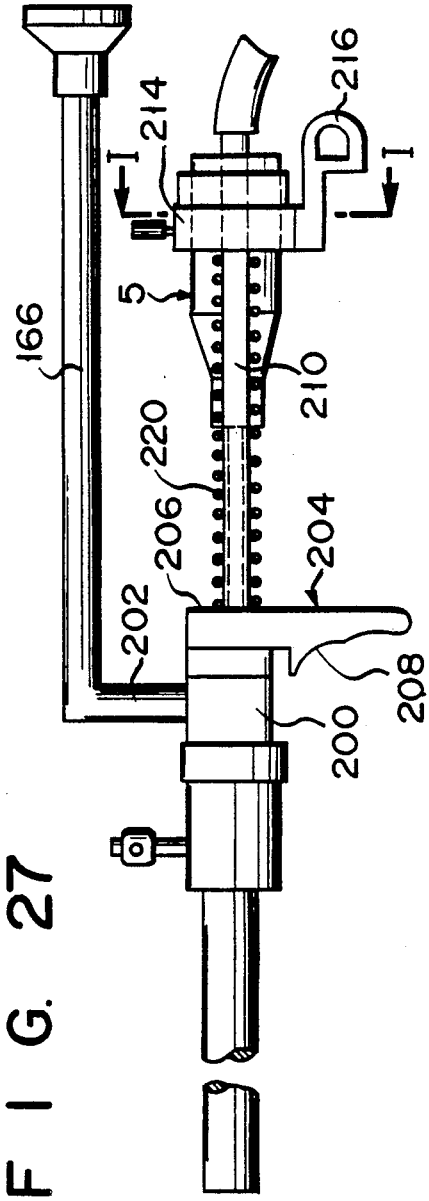
FIG. 26
FIG. 27

MEDICAL TREATMENT DEVICE UTILIZING ULTRASONIC WAVE

BACKGROUND OF THE INVENTION

A. Field of the Invention

The present invention relates to a medical treatment device utilizing an ultrasonic wave and, more particularly, to a medical treatment device used, for example, for resecting a human tissue of interest or breaking a stone in a body cavity by ultrasonic vibrations.

B. Description of the Prior Art

Conventional resection treatment of a human tissue of interest is to cauterize the tissue of interest with an RF current to resect the tissue.

According to this treatment, however, the cauterized tissue is degenerated into whitish tissue, and thus it is difficult to judge the resection area. Therefore, the conventional treatment poses a problem wherein even normal tissue tends to be resected.

In order to solve the problem posed by the conventional treatment, another resection treatment with ultrasonic vibrations has been recently practiced by a treatment device using such vibrations. A conventional treatment device using ultrasonic vibrations is proposed in Japanese Patent Application No. 60-1201 (Japanese Patent Disclosure, Kokai, No. 61-159953). This treatment device comprises a probe, that is, a vibration transmission member which is made of a pipe or the like and can be inserted in a living organism, and an ultrasonic vibrator, that is, an ultrasonic vibration generating means connected to the proximal end of the probe through a horn. In order to resect the tissue of interest, the distal end of the probe is inserted in a body cavity through, e.g., an endoscope channel inserted in the body cavity, and the distal end is urged against the tissue. The distal end of the probe is then vibrated to resect the tissue of interest. This treatment can also be applied to break a stone in a body cavity.

In a treatment using the above ultrasonic treatment device, an operator can erroneously damage blood vessels, thereby causing bleeding. When bleeding occurs, the probe inserted in the body cavity is removed, and a hemostatic instrument is inserted in the body cavity.

According to this conventional treatment, every time bleeding occurs, the instrument must be replaced, and the replacement operation is burdensome.

As disclosed in Japanese Patent Disclosure No. 52-93 (USP No. 3,990,452, DE 2626 373 132), a probe having a bent portion at its distal end is mounted on a treatment device utilizing ultrasonic vibrations. This device is used in a treatment. Vibrations having a predetermined amplitude are transmitted from an ultrasonic vibration generating means to the distal end of the probe, and the vibration frequency is controlled such that the distal end of the probe serves as a portion having a largest vibration magnitude, that is, a loop of the vibration. The treatment device is used as a device for resection of, e.g., tissue to be cured, by utilizing ultrasonic vibrations at the distal end of the probe.

A device with a probe having a bent portion at its distal end can be conveniently used in a limited body cavity and can be easily operated. However, the distal end of the probe is vibrating in only one direction, and thus reduces the capacity for resecting the tissue in a living organism or breaking a stone therein. Therefore, a strong demand has arisen for a treatment device utilizing ultrasonic vibrations having a high resection or breaking capacity.

SUMMARY OF THE INVENTION

It is an object of the present invention to provide a treatment device utilizing ultrasonic vibrations, wherein a probe inserted in a body cavity can be effectively utilized and complicated treatments can be provided by the distal end of the probe.

In order to achieve the above object of the present invention, there is provided a treatment device, comprising:

means for generating ultrasonic vibrations;

a horn connected to the ultrasonic vibration generating means;

a casing for accommodating the ultrasonic vibration generating means and the horn;

a probe, connected to a front portion of the horn, for transmitting ultrasonic vibrations generated by the ultrasonic vibration generating means, and having a distal end; and a power source unit for supplying a drive voltage to the ultrasonic vibration generating means, the power source unit having an oscillator for generating a frequency signal for vibrating the probe, and means for switching the oscillation frequency between a frequency for causing the distal end of the probe to serve as a loop of vibration and a frequency for causing the distal end of the probe to serve as a node of vibration.

A treatment device according to the present invention comprises means for switching the oscillation frequency of the ultrasonic vibration generating means, that is, a vibrator. The oscillation frequency of the vibrator is switched between a frequency, for causing the distal end of the probe to serve as a loop of vibration and a frequency for causing the distal end to serve as a node of vibration. A straight probe is attached to the vibrator, and the distal end of the probe is vibrated as a node of vibration, thereby causing the probe to be vibrated with ultrasonic waves. The distal end of the probe is heated, a bleeding tissue portion is cauterized and bleeding is stopped. Therefore, in the treatment device according to the present invention, resection and hemostasis of tissue can be performed by a single probe in the treatment device according to the present invention.

A probe having a bent portion at its distal end is attached to the vibrator, and the probe is vibrated with ultrasonic waves such that the distal end or the bent portion of the probe serves as a loop of vibration. The vibration direction of the distal end of the probe can be changed as needed. Therefore, the treatment device according to the present invention can effectively resect the tissue of interest.

BRIEF DESCRIPTION OF THE DRAWINGS

FIGS. 10 and 11 are views showing vibration waveforms of the probe;

FIGS. 12 to 14 are cross-sectional views showing modifications of the vibration generator in the treatment device shown in FIG. 9;

FIGS. 15 and 16 are cross-sectional views showing modifications of a vibration generator rear portion of the medical treatment device shown in FIG. 9;

FIG. 17 is a partially cutaway side view schematically showing a safety unit in the medical treatment device shown in FIG. 9;

FIG. 21 is a partially cutaway side view showing part of the resectoscope incorporating the medical treatment device according to the present invention;

FIGS. 22 to 25 are partial views showing working element portions of the resectoscope;

FIG. 26 is a partially cutaway sectional view showing a second structure of a resectoscope incorporating the medical treatment device according to the present invention;

FIG. 27 is a side view showing a third structure of the resectoscope;

DETAILED DESCRIPTION OF THE PREFERRED EMBODIMENTS

Preferred embodiments of the present invention will be described with reference to the accompanying drawings.

Figure 1:
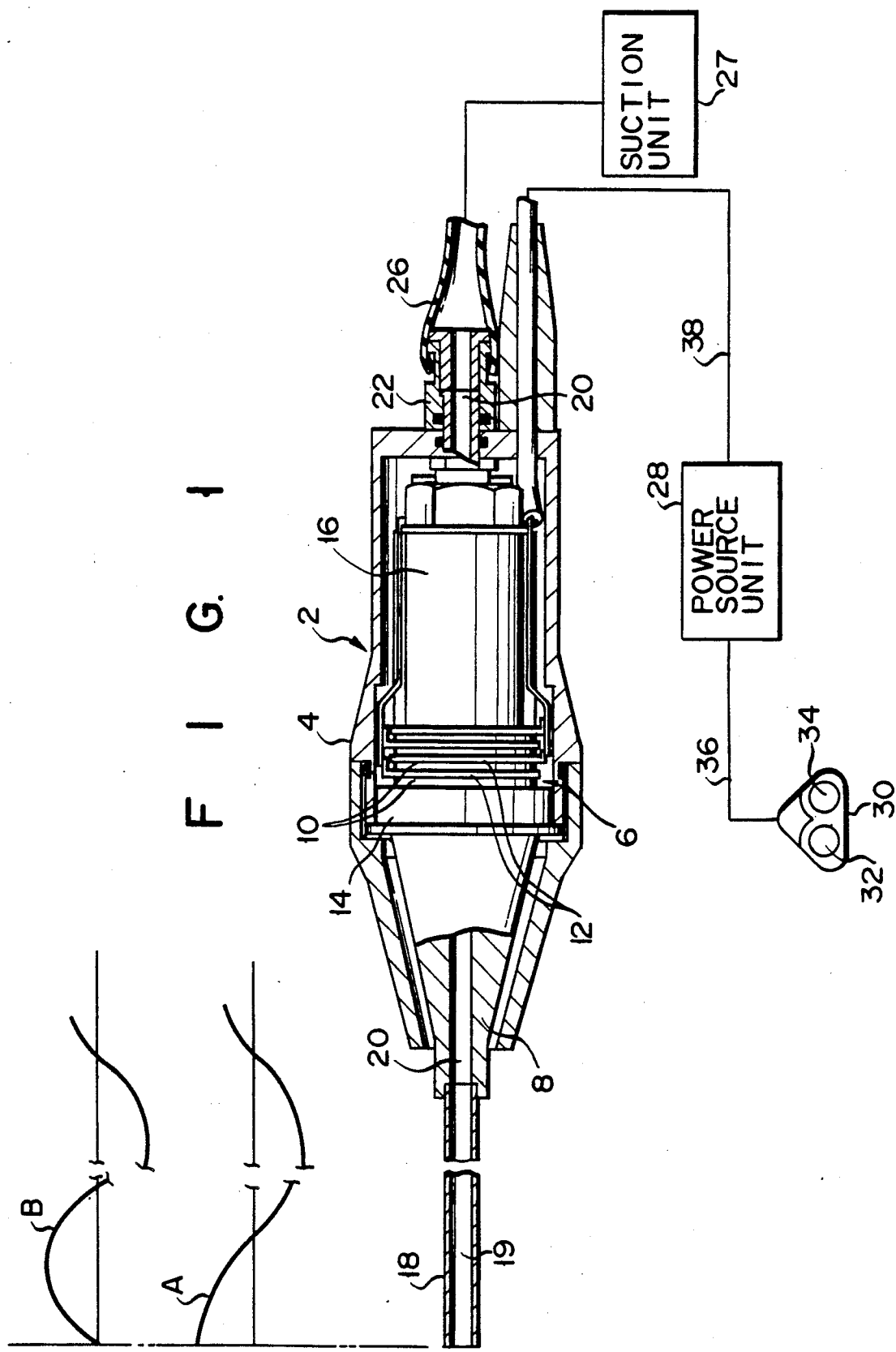
FIG. 1 is a partially cutaway side view schematically showing a medical treatment device utilizing ultrasonic waves according to a first embodiment of the present invention, the medical treatment device being illustrated together with vibration waveforms of a probe included therein.
Figure 3:
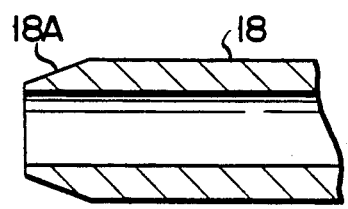
FIGS. 3 and 4 are sectional views showing the distal end portion of the probe in the medical treatment device shown in FIG. 1.
Figure 4:
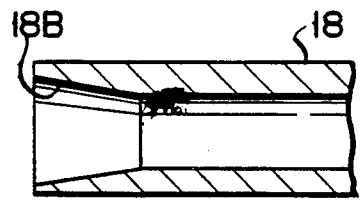

FIG. 1 shows a medical treatment device utilizing an ultrasonic wave according to an embodiment of the present invention. The ultrasonic treatment device comprises handle section 2 integrally formed with outer case 4. Ultrasonic vibrator 6 is housed inside case 4 to generate an ultrasonic vibration. Conical horn 8 is disposed inside the distal end portion of outer case 4. Vibrator 6 comprises a Langevin type vibrator. In the Langevin type vibrator, a plurality of piezoelectric elements 10 and a plurality of electrode plates 12 are alternately arranged. The alternate arrangement is clamped between front and rear metal blocks 14 and 16. Horn 8 is connected to the front surface of block 14. For example, pipe-like probe 18 made of, e.g., β-titanium alloy (Ti-15Mo-5Zn-3Al, Ti-15V-3Al-3Sn-3Cr, Ti-4Al-22V or Ti-3Al-3V-6Cr-4Mo-4Zr) is mounted at the distal end of horn 8, serving as a vibration transmission member. An ultrasonic vibration generated by ultrasonic vibrator 6 is transmitted to the distal end of probe 18. Probe 18 has through-hole 19, and path 20 communicating with hole 19 is constituted by various members inside case 4. Path 20 and through-hole 19 constitute a suction path for drawing resected tissue from the opening of the distal end of probe 18. Suction unit 27 is connected to suction port member 22 at the rear end portion of path 20, through suction tube 26. The distal end portion of probe 18 is tapered toward its distal end such that the thickness of the pipe is decreased toward the distal end. As shown in FIG. 3, for example, tapered portion 18A is formed on the outer surface of the distal end of pipe 18. Alternatively, as shown in FIG. 4, tapered portion 18B is formed on the inner surface at the distal end thereof. Therefore, vibration of a large magnitude can be obtained at the distal end of probe 18 by a change in sectional area of pipe 18.

The ultrasonic treatment device comprises power source unit 28 and foot switch 30. Switch 30 comprises, for example, ON/OFF switch 32 and frequency selection switch 34, and is connected to the input terminal of power source unit 28 through cable 36. The output terminals of unit 28 are connected to each electrode plate 12 in ultrasonic vibrator 6 through cable 38.

Figure 2:
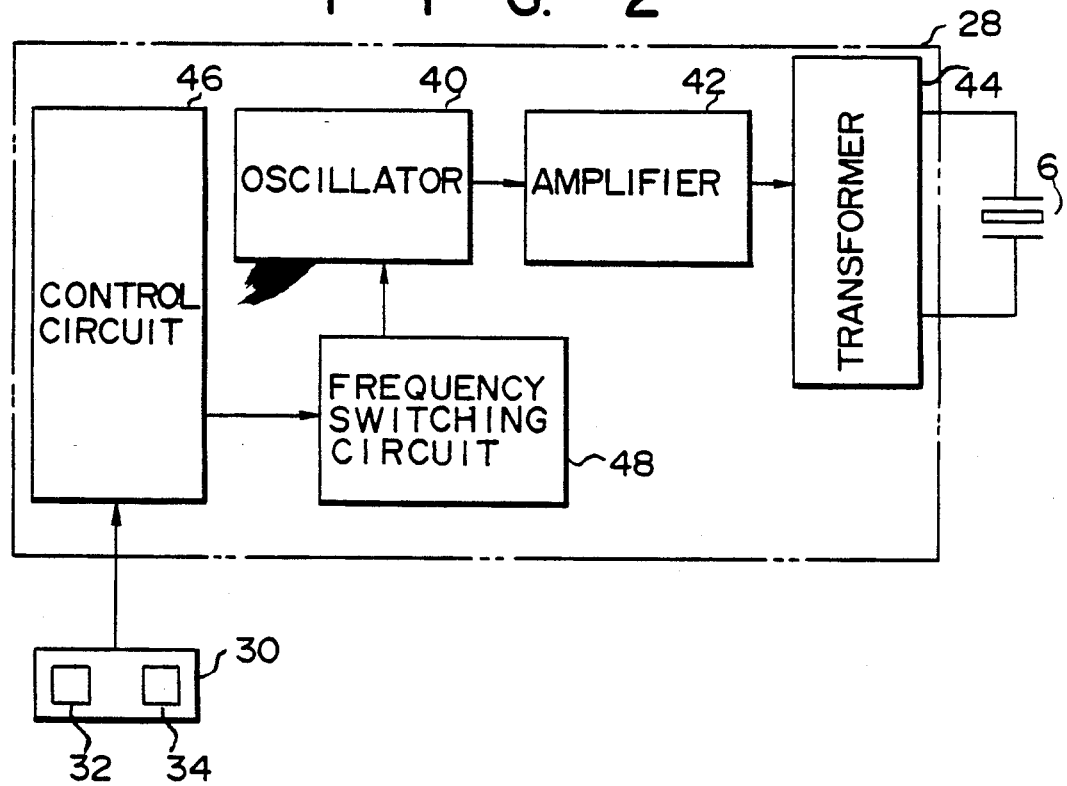
FIG. 2 is a block diagram of a power source unit of the medical treatment device shown in FIG. 1.

The circuitry of power source unit 28 will be described with reference to FIG. 2. Unit 28 comprises oscillator 40 for driving ultrasonic vibrator 6. Oscillator 40 is connected to oscillating transformer 44 through amplifier 42. Transformer 44 is connected to vibrator 6. Vibrator 6 can be driven in response to an RF drive voltage output from oscillator 40.

Control circuit 46 is connected to oscillator 40 through frequency switching circuit 48. Foot switch 30 is connected to the input terminal of control circuit 46. A switching signal from frequency selection switch 34 is supplied to frequency switching circuit 48 through control circuit 46. As a result, the oscillating frequency of oscillator 40 is switched between a frequency for maximally vibrating the distal end of the probe, that is, a frequency suitable for resection of a tissue or breaking of a stone, and a frequency at which the distal end of the probe does not vibrate.

Switching circuit 48 employs a circuit for causing oscillator 40 to oscillate at oscillating frequency A, at which the distal end of probe 18 serves as a loop of vibration and the distal end vibrates with a maximum amplitude, and at oscillating frequency B, at which the distal end of probe 18 serves as a node of vibration and does not substantially vibrate. Therefore, the two oscillating frequencies can be selectively used. For example, when switch 34 is turned off, switching circuit 48 selects frequency A at which the distal end of the probe 18 serves as a loop of vibration. However, when switch 34 is turned on, switching circuit 48 selects frequency B at which the distal end of probe 18 serves as a node of vibration. In this manner, the oscillating frequencies can be selectively switched upon operation of switch 34 in foot switch 30.

ON/OFF switch 32 is connected to control circuit 46, and power source unit 28 is turned on/off upon operation of switch 32. A driver for suction unit 27 is connected to control circuit 46.

The operation of the above ultrasonic treatment device will be described.

In order to resect, e.g., the prostate of a patient by using the ultrasonic treatment device, probe 18 is inserted in the ureter through a channel of an endoscope. The distal end of the probe is urged against the region of interest of a prostate portion. Thereafter, the operator operates ON/OFF switch 32 by foot, and ultrasonic vibrator 6 is driven to generate a wave having oscillation frequency A. Therefore, an ultrasonic vibration, for causing the distal end of the probe to serve as a loop of vibration, is transmitted to probe 18. Ultrasonic vibrations having a maximum amplitude at the distal end of probe 18 are transmitted to the region of interest, and the tissue is resected. The resected tissue can be discharged outside the body through a suction path by suction unit 27, synchronously operated with vibrator 6.

When bleeding occurs during the resection, the operator operates frequency selection switch 34 to switch the oscillating frequency from frequency A to frequency B at which the distal end of probe 18 serves as a node of vibration. A bleeding portion is then subjected to hemostasis by heat generated at the distal end of probe 18.

The principle of heat generation at the distal end of probe 18 will be described below. When probe 18 is vibrated by ultrasonic vibrations, a probe portion serving as the node of vibration is neither changed in position nor has an amplitude. A maximum bending stress acts on the node portion, and the portion is heated. The node can correspond to the distal end of probe 18 upon switching of the frequencies. This heat cauterizes the bleeding portion.

The ultrasonic treatment device according to the present invention causes one probe to allow both a resection and hemostasis. Therefore, two probes need not be prepared, and the probes need not be replaced for different applications. The above operation can also be performed as a treatment for breaking a stone in a body cavity by ultrasonic vibrations.

A switch (not shown) in place of foot switch 30 may be mounted on power source unit 28, and the oscillating frequency may be switched by this switch.

A modification of the probe in the ultrasonic treatment device according to the first embodiment of the present invention will be described below.

Figure 5:
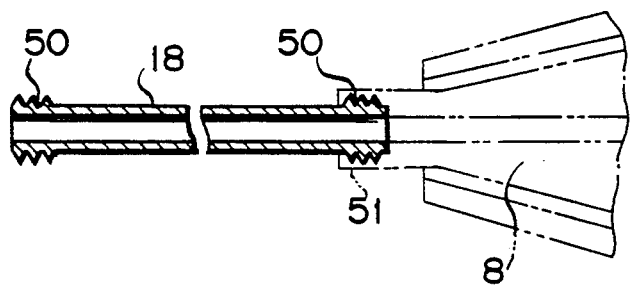
FIG. 5 is a sectional view showing a first modification of the probe.

FIG. 5 shows a modification of probe 18. In this modification, male threaded portions 50 are respectively formed at both end portions of probe 18. Female threaded portion 51 corresponding to threaded portion 50 is formed at the distal end portion of horn 8. Either end of probe 18 can be attached to horn 8.

Figure 6:
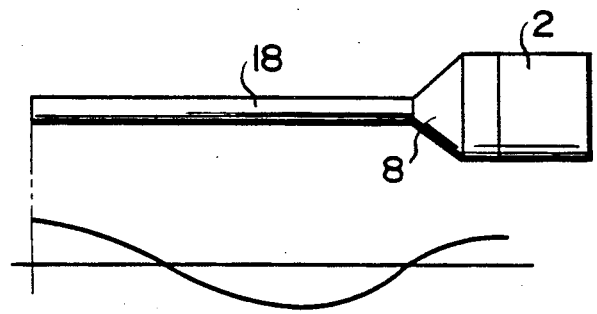
FIG. 6 is a side view showing a vibration generator together with vibration waveforms of the probe.

As shown in FIG. 6, a treatment is performed at a frequency for causing the distal end of probe 18 to serve as the loop of vibration in the ultrasonic treatment device. As described with reference to the above embodiment, the maximum stress is generated at a vibration node portion. In addition, the position of the node portion is not changed, and the stress is concentrated thereon. Therefore, damage by fatigue occurs in the node portion of probe 18, thus degrading its durability. In the above modification, either end of the probe can be attached to the horn. The mounting direction can be reversed to change the node portion position to the loop portion position and vice versa. As a result, durability of the probe can be improved.

Figure 7:
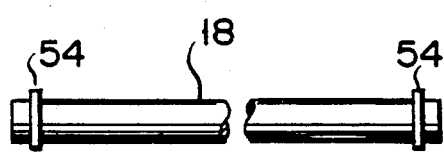
FIG. 7 is a side view showing a second modification of the probe.
Figure 8:
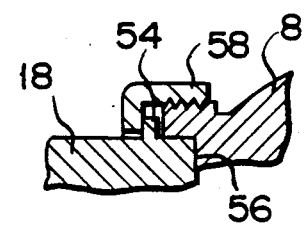
FIG. 8 is a sectional view showing a connection between the probe and a horn.

FIG. 7 shows another modification of the probe in an ultrasonic treatment device according to the first embodiment. In this modification, flanges 54 are respectively formed on the outer surfaces of both ends of probe 18. As shown in FIG. 8, recess 56 corresponding to the end of probe 18 is formed at the distal end portion of horn 8, as shown in FIG. 8. Recess 56 and the probe end portion are coupled by annular fastening screw 58 fixed on the outer surface of probe 18. One end portion of probe 18 is inserted in recess 56 of horn 8, and screw 58 is threadably engaged with the male threaded portion formed at the distal end of horn 8. The flange 54 is urged against horn 8, and probe 18 can be fixed to horn 8.

Figure 9:
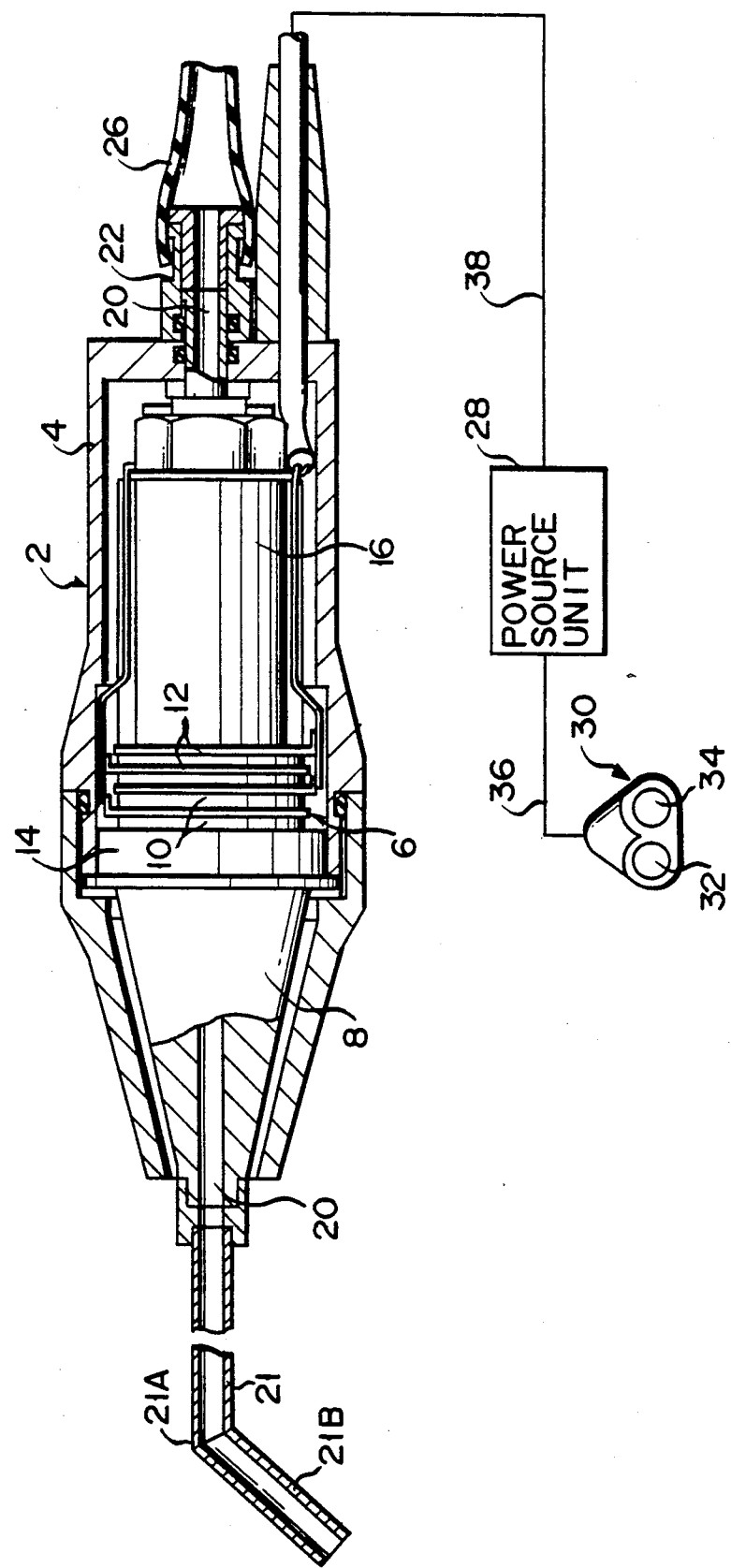
FIG. 9 is a partially cutaway side view schematically showing a medical treatment device utilizing ultrasonic waves according to a second embodiment of the present invention.

An ultrasonic treatment device according to a second embodiment of the present invention will be described with reference to FIGS. 9 to 11.

In this embodiment, probe 21 having bent portion 21A is attached to the front portion of horn 8. Ultrasonic vibrations generated by vibrator 6 are transmitted to distal end portion 21B of probe 21. This device comprises frequency selection circuit 48 for selecting frequency A at which distal end portion 21B of probe 21 is maximally vibrated and frequency B at which bent portion 21A of probe 21 is maximally vibrated.

Frequency selection circuit 48 comprises a circuit for selecting oscillating frequency A at which bent portion 21A serves as a node of vibration, the distal end of probe 21 serves as a loop of vibration, and the distal end of the probe vibrates at a maximum amplitude, as shown in FIG. 10, or oscillating frequency B at which bent portion 21A serves as a loop of vibration and is vibrated at a maximum magnitude, as shown in FIG. 11. Therefore, the two oscillating frequencies of oscillator 40 can be selectively used.

The operation of the ultrasonic treatment device according to the second embodiment will be described below.

Distal end 21B of probe 21 is urged against the tissue of interest before it is resected. When the operator operates ON/OFF switch 32 by foot, ultrasonic vibrator 6 is driven to generate a wave having frequency A. As shown in FIG. 10, distal end 21B of probe 21 serves as the loop of vibration and bent portion 21A serves as a node of vibration, and this vibration is transmitted to probe 21. The vibration wave, that is, the standing wave causes the distal end of probe 21 to vibrate in a bending direction of arrow X in FIG. 10 since distal end 21B of probe 21 serves as the loop of vibration.

When it is difficult to resect the tissue during the surgical operation, the operator operates frequency selection switch 34 in foot switch 30 by foot, and oscillating frequency A is changed to oscillating frequency B at which bent portion 21A serves as a loop of vibration, as shown in FIG. 11. Bent portion 21A is vibrated at a maximum amplitude at oscillating frequency B. Therefore, distal end 21B of probe 21 is vibrated in the axial direction, i.e., in a direction of arrow Y in FIG. 11. By this operation, the resection direction at distal end 21B of probe 21 is changed to effectively resect the tissue of interest.

As is apparent from the above description, the tissue of interest can be resected by changing vibration directions to achieve effective resection operations. Therefore, treatment efficiency of ultrasonic vibrations can be further improved.

Modifications of the vibration generator, or generating section, in the ultrasonic treatment device will be described with reference to FIGS. 12 to 14.

FIG. 12 shows a first modification of vibration generator 5. Ultrasonic vibrator 6 is arranged in generator 5. Conical horn 8 is mounted at the front portion of vibrator 6. Bolt 60 is threadably engaged with the rear portion of horn 8. This ultrasonic vibrator 6 is a Langevin type vibrator. Vibrator 6 comprises bolt 60. Piezoelectric element 10 and electrode plates 12A and 12B, and metal block 62, each of which has a bolt insertion hole, and these members all surround bolt 60. These members are clamped between horn 8 and nut 64, both of which are threadably engaged with both ends of the bolt, respectively. Recess 65 is formed between bolt 60 and the bolt insertion holes of piezoelectric element 10, electrode plates 12A and 12B, and block 62. Therefore, the bolt is insulated from the above members through an air layer. A probe, that is, a transmission member made of a pipe is connected to the distal end of horn 8 connected to vibrator 6. The ultrasonic vibration generated by vibrator 6 is transmitted to the distal end of probe 18.

In this modification, ceramic washers 66A and 66B are inserted between horn 8 and electrode plate 12A and between metal block 62 and electrode plate 12B. Washers 66A and 66B do not absorb vibrations but transmit them to the probe efficiently. In addition, washers 66A and 66B insulate electrode plates 12A and 12B from horn 8 and block 62, respectively, thereby perfectly insulating plates 12A and 12B in cooperation with recess 65.

Cords 68 are respectively connected to electrode plates 12A and 12B, and a drive voltage is supplied from the power source unit to plates 12A and 12B through cords 68.

When the ultrasonic treatment device is used and a current leaks from electrode plates 12A and 12B, a leakage current may be supplied to probe 18.

In the device of this modification, however, ceramic washers 66A and 66B are arranged in the path between the electrodes and probe 18. In addition to the air insulating layer, electrode plates 12A and 12B can be completely insulated. Even if a current flows from the electrode plates, it does not flow into probe 18, thereby preventing the patient from receiving an electric shock.

FIG. 13 shows a second modification of the vibration generator. In this modification, insulating ceramic washer 12A is arranged only between horn 8 and electrode plate 12A. In this case, bolt 60 is made of an insulating material, e.g., a ceramic material.

FIG. 14 shows a third modification of the vibration generator. In this modification, insulating ceramic washers 66A and 66B are arranged in the same manner as in the first modification. At least an outer surface portion of bolt 60, which is brought into contact with electrode plates 12A and 12B, is covered with insulating coating 70. Therefore, electrode plates 12A and 12B are completely insulated. With this structure, the electrode plates are more thoroughly insulated as compared with the above modifications.

In all the modifications, a ceramic material is used as the insulating member. However, the insulating material is not limited to the ceramic material. Any insulative material which does not absorb vibrations but transmits them can be used. The end face of the horn may be covered with an insulating coating, instead of using insulating washers.

Modifications of the rear portion of the vibration generator will be described with reference to FIGS. 15 and 16, respectively. In the modification of FIG. 15, the inner hole of probe 18, connected to horn 8, communicates with those of ultrasonic vibrator 6 and horn 8 to constitute linear discharge path 20. Linear pipe 72, having a treatment tool insertion port, is attached to the rear portion of case 4. Pipe 72 is connected to discharge path 20. The central axis of inner hole 74 of pipe 72 is aligned with a line extending from the central axis of discharge path 20. Cock 76 is attached to pipe 72 to open or close it. In this case, cock 76 is attached to the distal end portion of the extended portion of pipe 72. Cock 76 has valve body 78 with communication hole 80. Operation lever 82 connected to valve body 78 is operated to open/close cock 76, that is, the valve.

Discharge connection portion 86, branched from pipe 72 consisting of discharge path 20 and inner hole 74, is formed in pipe 72 in front of cock 76. Discharge tube 88 is connected to connecting portion 86.

In the treatment device of this modification, when opening/closing cock 76 is closed, a liquid in a body cavity at the time of resection or lithotomy with ultrasonic vibrations, and resected or broken tissue can be discharged outside through tube 88 connected to connecting portion 86.

When the operator uses the treatment tool, cock 76 is opened to insert a treatment tool into inner hole 74 of pipe 72. Since inner hole 74 and discharge path 20 are linear, even a hard treatment tool can be easily inserted.

FIG. 16 shows another modification. Ultrasonic vibration generator 5 of this modification has rotary member 90 rotatably mounted to case 4. Rotary member 90 is mounted to be rotatable about the central axis of discharge path 20. More specifically, the device comprises connecting pipe 92 which extends from the rear end portion of case 4 and communicates with discharge path 20. Rotary member 90 is mounted on the extended portion of pipe 92, and linear end pipe 84 is connected to the rear portion of rotary member 90. Pipe 84 has a treatment tool insertion port. The central axis of inner hole 74 of pipe 84 is aligned with the axis of discharge path 20. Discharge pipe 96 corresponding to the discharge tube in the above modification and power source cord 68 for supplying a voltage to vibrator 6 are mounted in rotary member 90.

Connecting ring 98, electrically connected to ultrasonic vibrator 6, is mounted on the outer surface of connecting pipe 92, as shown in FIG. 16. Contact pin 100 mounted on rotary member 90 is in contact with connecting ring 98. Pin 100 is connected to power source cord 68. In this modification, discharge pipe 96 and power source cord 68 are mounted in rotary member 90. Even if ultrasonic vibration generator 5 is rotated, discharge pipe 96 and power source cord 68 do not catch each other. In the above modifications, debris can be discharged through tube 88 or discharge pipe 96. In addition, a rigid treatment tool can be especially used.

A safety unit in the ultrasonic treatment device according to the present invention will be described with reference to FIGS. 17 to 20.

The vibration generator in the treatment device, as shown in FIG. 17, comprises elongated guide pipe 102 and large-diameter handle 2 connected to the rear end of pipe 102. A vibrator as a vibrating means is housed in handle 2. Elongated vibration rod 108 inserted in guide pipe 102 is vibrated by vibrator 106.

Vibrator 106 comprises magnetostrictive vibrator element 110 made of, e.g., nickel, alphero, or ferrite, and coil 112 surrounding element 110. An RF current supplied from external RF oscillator 114 to coil 112 oscillates element 110, thereby constituting a transducer.

Magnetostrictive element 110 is connected to vibration rod 108 through coupling 116. Rod 108 reciprocally vibrates together with element 110 along the longitudinal direction. Hollow portion 103 between the outer surface of rod 108 and guide pipe 102 is connected to water supply tube 118 near the rear end of pipe 102. Physiological saline or the like is supplied from a water supply means (not shown) to the distal end of vibration rod 108 through hollow portion 103. Tissue resected from prostate 120 is drawn together with saline or the like by a suction means (not shown) through hollow portion 109 in vibration rod 108 and suction tube 122.

A safety unit is arranged in the treatment device not to resect muscle tissue 124 when prostate 120 is partially resected by vibration rod 108.

The safety device will be described in detail below.

An annular recess or groove is formed on the outer surface at the rear end of vibration rod 108 adjacent to coupling 116. Annular permanent magnet 126 is fixed in the groove. Coil 128 is mounted at a position opposite to magnet 126 in the inner wall of case of handle 2. A current induced by coil 128 allows detection of a change in vibration frequency of rod 108.

Coil 128 is connected to the input terminal of frequency detector 130. The output terminal of detector 130 is connected to one input terminal of comparator 132. Detector 130 comprises, e.g., a waveshaper, a counter, and a D/A converter. An output voltage from the D/A converter is supplied to one input terminal of comparator 132 and is compared with a reference voltage supplied to the other input terminal of comparator 132. When the input voltage is lower than the reference voltage, the output of comparator 132 becomes high, and alarm unit 134, a buzzer or an LED, is driven. 0-rings 136A and 136B are mounted at the connecting portion of the proximal portion of guide pipe 102. Thus, the vibration generator has a waterproof structure. 0-ring 136C is mounted on the outer surface of coupling 116 near the connecting portion of suction tube 122.

The operation of the safety unit will be described below.

An endoscope having a detachable optical observation pipe (not shown) is inserted in a body cavity, and a portion to be resected is checked. The observation pipe is removed and guide pipe 102 is inserted in the channel in which the optical observation pipe has been inserted. The power switch of RF oscillator 114 is turned on to supply an RF current to coil 112 in vibrator 106. Magnetostrictive element 110 is vibrated, and vibration rod 108 connected thereto is also vibrated along the longitudinal direction thereof. Vibration rod 108 is moved forward and abuts against prostate 120. A portion of the prostate is resected. The resected tissue is drawn by a suction means together with water supplied through water supply tube 118, through hollow portion 109 in vibration rod 108.

When vibration rod 108 is brought into contact with tissue to resect it, the physical properties of the tissue cause a change in load of vibration rod 108. For this reason, the vibration frequency of rod 108 is changed. However, in order to resect the tissue of prostate 120, the load of rod 108 is small, and a change in vibration frequency is small. An output voltage from comparator 132 is kept at low level, and it is thus understood that the device is normally operated. When rod 108 resects prostate 120 and reaches muscle tissue 124 near prostate 120, a load acting on vibration rod 108 is gradually increased. The change in frequency is detected by detector 130. When rod 108 comes closer to tissue 124, an output voltage from detector 130 exceeds the reference voltage as an allowable value. The output voltage from comparator 132 is set at a high level, and alarm unit 134 is energized to generate a buzzer tone or turn on an alarm LED.

Accidental resection of tissue other than a portion to be resected can therefore be completely prevented.

In the above device, the change in vibration frequency is detected. However, a change in differential of the vibration frequency may be detected. Alternatively, an amplitude detecting means may be arranged in place of vibration frequency detecting means. In order to change the amplitude of the rod to operate the alarm unit, an envelope of an electrical signal from the detector is detected, and an envelope value is input to one input terminal of comparator 132. If the envelope signal has a small magnitude, an amplifier is inserted between the detector and comparator 132.

The power switch of oscillator 113 may be kept off so as not to supply the output current from RF oscillator 114 to vibrator 106 whenever alarm unit 134 is energized. Comparator 132 may comprise a window comparator. In this case, when the detected signal voltage has a higher magnitude than that of a predetermined alarming level, RF vibration of rod 108 is automatically stopped. The alarm signal level can be set according to the physical properties of the tissue to be resected.

Figure 18:
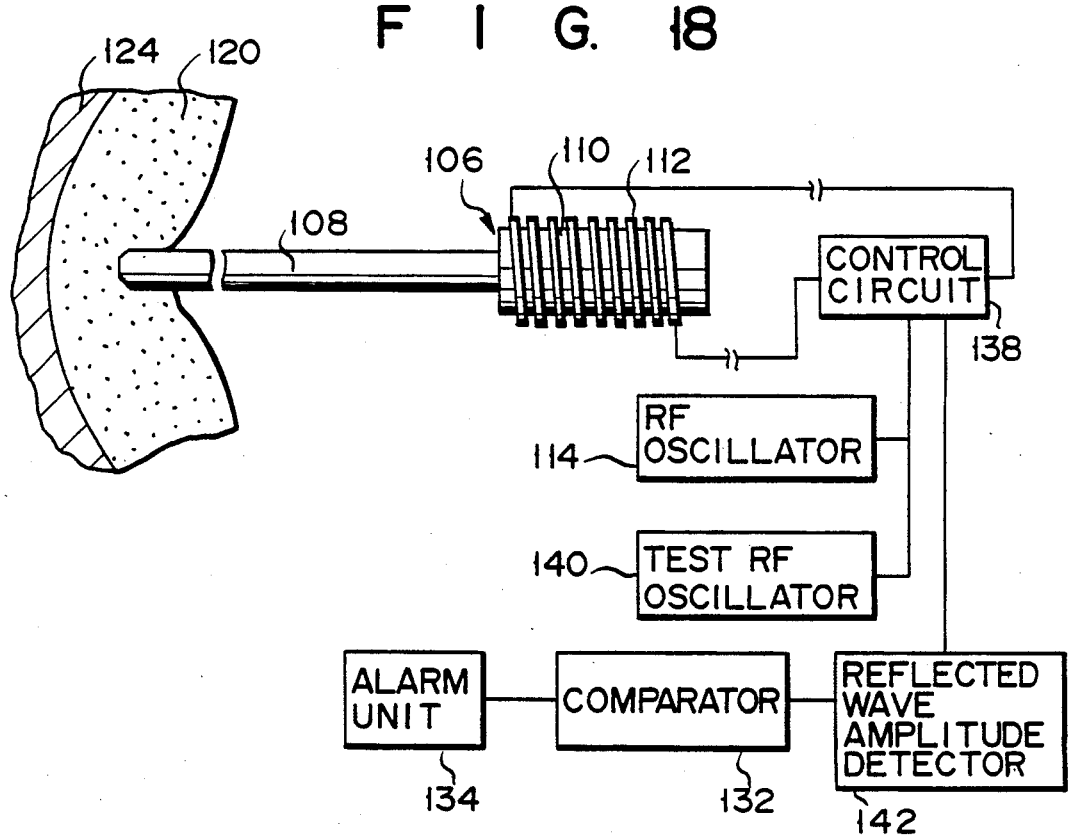
FIG. 18 is a block diagram schematically showing a second structure of the safety unit.

FIG. 18 schematically shows another embodiment of the safety unit. A safety means of this embodiment does not comprise a magnet and coil 128, both of which constitute a vibration frequency detecting means. Coil 112 in vibrator 106 is connected to a resection RF oscillator 114 through control circuit 138, to test RF oscillator 140, and to reflected wave amplitude detector 142 through control circuit 138. Detector 142 is connected to alarm unit 134 through comparator 132.

Figure 19:
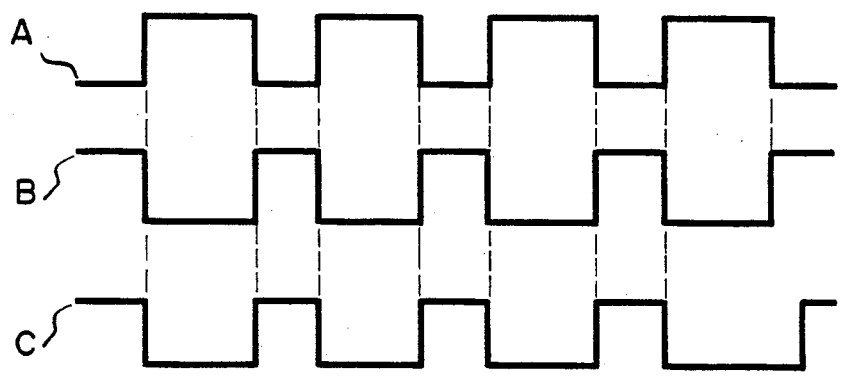
FIG. 19 is a timing chart showing waveforms of signals generated by an oscillator in the safety unit shown in FIG. 18, and a waveform of a reflected wave.

As shown in FIG. 19, RF oscillator 114 generates resection RF current pulses A, and test RF oscillator 140 generates test RF current pulses B for checking the off period of pulses A. An amplitude level of an echo as a reflected wave is input to reflected wave amplitude detector 142 through control circuit 138. Alarm unit 134 generates an alarm or the resection RF oscillating current is interrupted when the amplitude of reflected wave C in FIG. 19 exceeds the allowable value.

In this embodiment, permanent magnet 126 and coil 128 need not be included, thus simplifying the structure.

Figure 20:
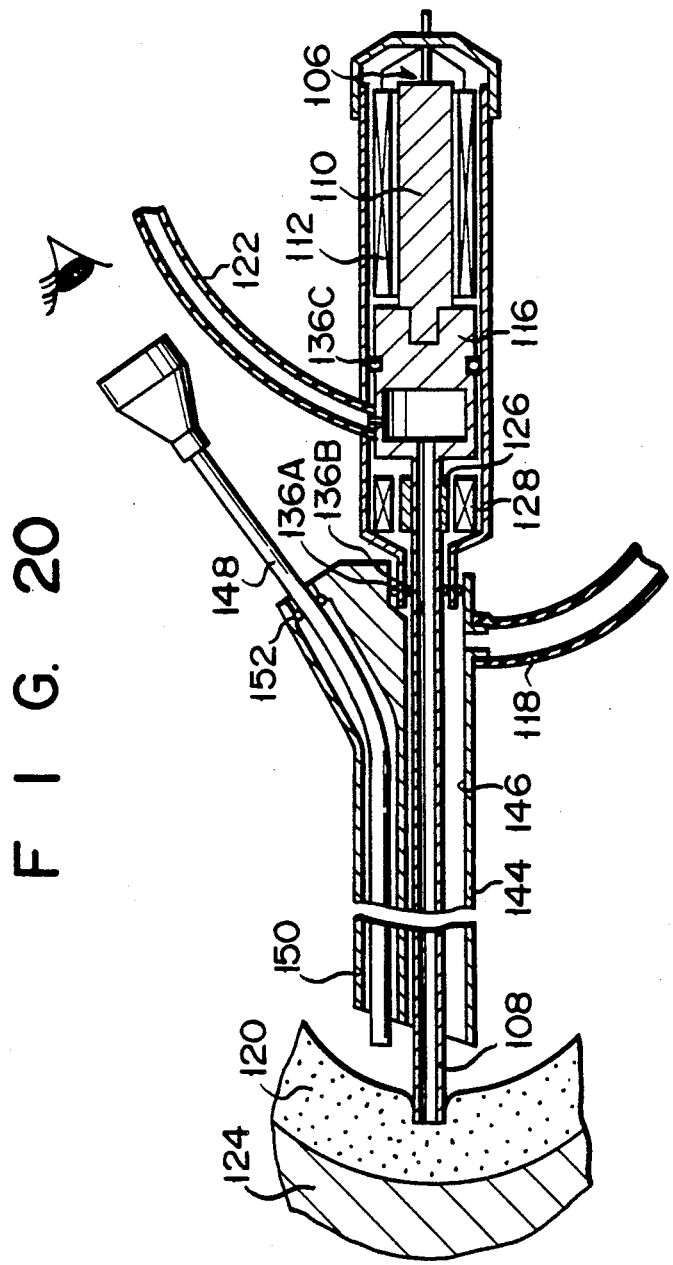
FIG. 20 is a cross-sectional view schematically showing a resectoscope built into a treatment device having a safety unit.

FIG. 20 shows an endoscope, or a resectoscope, incorporating a treatment device having the safety unit described above. The resectoscope comprises guide pipe 144, having channel 146 through which a treatment tool is inserted, and channel 150 in which optical observation pipe 148 is inserted. O-ring 152 for assuring a waterproof property is mounted near the rear end of channel 150 through which pipe 148 is inserted. Magnet 126 is fixed on the outer surface of vibration rod 108. Vibration rod 108 is integrally formed with coupling 116.

The operator can resect the tissue of interest while observing that portion with optical observation pipe 148. Therefore, a more safe surgical operation can be performed.

The inner hole of channel 146 or vibration rod 108 is not used as a water supply or suction path. In this case, channel 150 of the optical observation pipe can be used as the water supply or suction path. Therefore, vibration rod 108 is not limited to a tubular member, but can be a solid rod.

A member obtained by stacking plate members is used to constitute magnetostrictive element 110 in vibrator 106 so as to reduce power loss caused by an eddy current. Furthermore, a magnetic field generated by vibrator 106 is not constituted by a rod-like open loop, but constituted by a closed loop to increase a magnetic force of vibrator 106. In addition, a vibrator utilizing a magnetostrictive phenomenon, e.g., coil 112 with a permanent magnet, may be used in a vibrator designed to be vibrated with an RF current. Alternatively, a pressure vibrator may be used as the vibrator.

An endoscope, or a resectoscope, having the ultrasonic treatment device according to the present invention will be described with reference to FIGS. 21 to 25.

The resectoscope shown in FIG. 21 comprises sheath 160 as a scope body. Metal piece 162 is attached to the rear end of sheath 160. A pair of through-holes 164 are formed in metal piece 162. Optical observation pipe 166 is slidably inserted in one through-hole 164. Probe 18 is slidably inserted in the other through-hole 164. Eyepiece 168 is mounted on the rear end portion of optical observation pipe 166 extending backward from metal piece 162. Obliquely bent portion 18D is formed at the rear end portion of probe 18. Vibration generator 5 having an ultrasonic vibrating element is connected to the rear end portion of probe 18. Probe 18 can be vibrated by generator 5 having the ultrasonic vibrating element.

Figure 25:
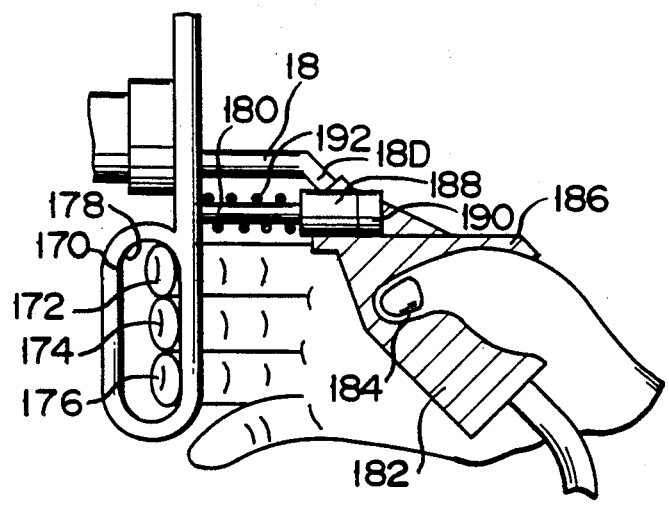

First finger handle 170 is connected and fixed to the recess of metal piece 162. Finger hole 178 is formed in finger handle 170 so that first finger 172, second finger 174 and third finger 176 can be inserted in hole 178, as shown in FIG. 25. A pair of guide rods 180 extend backward from finger handle 170. Case 182 having vibration generator 5 therein is slidably mounted on rod 180. Second finger handle, that is, projection 186 is formed in case 182 to rest the base of thumb 184 on projection 186. A pair of bosses 186 are arranged in front of case 182 and are slidably mounted on guide rod 180. Stopper 190 is screwed to an end face of guide rod 180, as shown in FIG. 22. Stopper 190 serves to prevent accidental removal of case 182 from guide rod 180. Spring 192 is mounted on guide rod 180 so as to bias case 182 in a direction to withdraw probe 18.

When the resectoscope having the above-mentioned structure is used, the operator hooks fingers 172, 174 and 176 of his one hand at hole 178, and hooks projection 186 at the base of his thumb 184. Therefore, the operator can hold the resectoscope with one hand.

Figure 23:
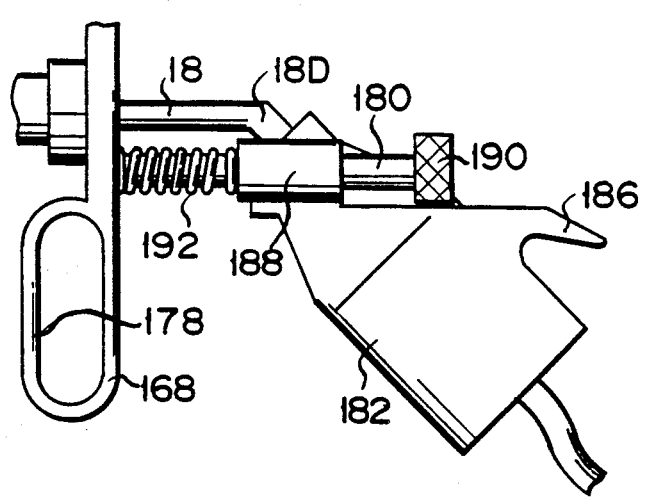
Figure 24:
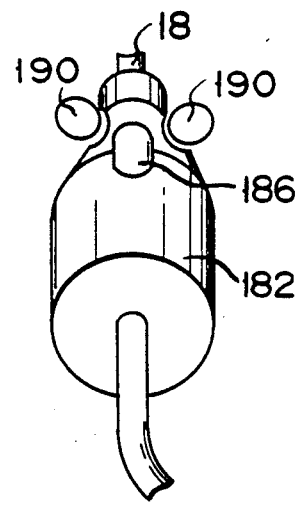

In order to project the distal end of probe 18 from the distal end face of sheath 160 while the operator holds the resectoscope with one hand, he holds the resectoscope tighter. As shown in FIG. 23, case 182 is moved forward along guide rod 180 against the biasing force of spring 192. Probe 18 is then moved together with case 182 and extends outside from the distal end face of sheath 160. When the operator releases the holding force, case 182 is retracted by the force of spring 192, so that the distal end of probe 18 extending outside from the distal end face of sheath 160 is retracted, as shown in FIG. 22. In this manner, the operator can reciprocate probe 18 while holding the resectoscope with one hand.

The operator can use the free hand to perform other operations associated with a surgical operation. Bent portion 18D is formed at the rear end portion of probe 18. Vibration generator 5 is connected to the end portion of bent portion 18D. A distance between case 182 having generator 5 therein and eyepiece 168 of optical observation pipe 166 is sufficiently large, and operability of the resectoscope is good. Furthermore, since optical observation pipe 166 can be located near probe 18, the overall size of the resectoscope can be made compact.

A second structure of the resectoscope having the ultrasonic treatment device according to the present invention will be described with reference to FIGS. 26 to 30.

The resectoscope comprises sheath 160. Optical observation pipe 166 is inserted in sheath 160. The proximal portion of pipe 166 has connecting portion 200. Projection 202 serving as a first finger handle extends on the upper portion of connecting portion 200. Projection 202 is used to hold the operator's fingers. Connecting portion 200 is connected and fixed at the proximal end portion of sheath 160.

Working element 204 is fixed to the rear end face of connecting portion 200. Element 200 comprises attachment piece 206 fixed to the rear end face of connecting portion 200, second finger handle 208 disposed at a position vertically corresponding to projection 202 of pipe 166, and slide shaft 210 extending backward from connecting portion 200. These components are integrally formed.

As shown in FIG. 26, through-holes 212 are respectively formed in connecting portion 200 of optical observation pipe 166 and in attachment piece 206 of working element 204 attached to connecting portion 200. Probe 18 in the ultrasonic treatment device according to the present invention is inserted in sheath 160 through through-holes 212. The ultrasonic vibrating element is connected to the proximal end of probe 18, and probe 18 is vibrated by the ultrasonic vibrating element. Slider 214 is attached to working element 204. Vibration generator 5 is detachably mounted in the upper portion of slider 214, and finger handle 216 is formed at the rear portion thereof. Through-hole 218 is formed at the intermediate portion to slidably receive slide shaft 210. Spring 220 is mounted on shaft 210.

In the resectoscope having the structure described above, the thumb of one hand is held in rear finger handle 216, the first finger is held in projection 202 in optical observation pipe 166, and the second, third, and fourth fingers are held in second finger handle 208. When the operator holds the resectoscope tightly, the ultrasonic treatment device can be moved forward against the biasing force of spring 220.

Second finger handle 208 is disposed at a position vertically corresponding to projection 202 of optical observation pipe 16 in the resectoscope having the structure described above. The operator can hook the first finger on projection 202. Therefore, unlike in the resectoscope previously mentioned, the operator need not hook the first finger on second finger handle 208, and thus the length of handle 208 can be shortened. Second finger handle 208 does not interfere with rotation of the resectoscope, and operability of the resectoscope is not degraded.

Figure 28:
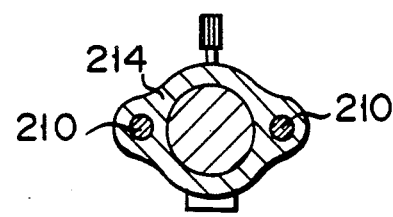
FIG. 28 is a longitudinal sectional view of the resectoscope in FIG. 27 taken along the line I—I thereof.

In the resectoscope shown in FIGS. 27 and 28, a pair of slide shafts 210 having the same axis as that of vibration generator 5 in the ultrasonic treatment device are arranged in working element 204. Therefore, as compared with a resectoscope having slide shaft 210 lower than generator 5, the profile can be reduced.

Figure 29:
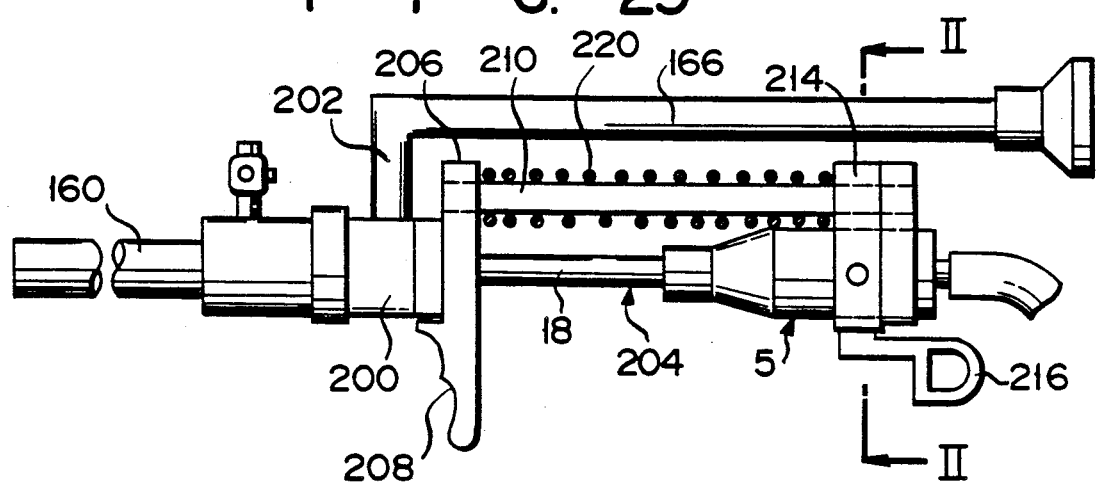
FIG. 29 is a side view showing a fourth structure of the resectoscope.
Figure 30:
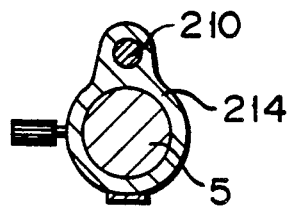
FIG. 30 is a longitudinal sectional view of the resectoscope in FIG. 29 taken along the line II—II thereof.

In the resectoscope shown in FIGS. 29 and 30, one slide shaft 210 is disposed above the axis of the vibration generator. With this structure, the overall size of the resectoscope can be reduced.

Rear finger handle 216 of the resectoscope having the above structure is preferably vertically formed below the center of gravity of vibration generator 5 having an ultrasonic vibrating element. With this arrangement, the operator can hold the resectoscope with one hand and can operate it with good balance and stability.

What is claimed is:

1. An ultrasonic treatment device, comprising:
   means for generating ultrasonic vibrations;
   elongated probe means having a distal end portion and a proximal end portion, said proximal end portion being connected to said ultrasonic vibration generating means, said probe means being vibrated by said ultrasonic vibration generating means for resecting a tissue contacting said distal end portion of said probe means;
   detecting means for detecting an amplitude variation or a frequency variation of vibration of said probe means arising from a physical property of the tissue contacted by the distal end portion of said probe means, and for producing a detection signal which is a function of the detected amplitude or frequency variation of vibration of said probe means;
   comparing means for comparing a level of said detection signal from said detecting means with a predetermined signal level and for generating a driving signal when the difference between said detection signal and said predetermined signal level exceeds a predetermined value; and
   safety means coupled to said comparing means for at least one of generating an alarm in response to said driving signal from said comparing means, and stopping a vibration of said probe means in response to said driving signal generated by said comparing means.

2. The device of claim 1, wherein said ultrasonic vibration generating means includes a horn connected to said proximal end portion of said probe means.

3. The device of claim 2, further comprising a casing means surrounding said ultrasonic vibration generating means and said horn.

4. The device of claim 2, wherein said ultrasonic vibration generating means and said probe means respectively define internal channels cooperatively coupled together to form a common channel, and further comprising means coupling said common channel to a suction unit.

5. The device of claim 2, wherein said elongated probe means has two ends, and further comprising disconnectable connecting means formed at both ends of said probe means, for selectively connecting each of said ends of said probe means to said horn, thereby permitting changing an attachment direction of said probe means.

6. The device of claim 5, wherein said connecting means at both ends of said probe means comprises screw means.

7. The device of claim 1, wherein said probe means has a bent portion at its distal end portion.

8. The device of claim 6, wherein said probe means has a bent portion at its distal end portion.

9. The device of claim 1, wherein further comprising a casing means surrounding said ultrasonic vibration generating means, and wherein said ultrasonic vibration generating means comprises a vibration element and electrode plates coupled to said vibration element, said vibration element and said electrode plates being insulated from said casing means by spacing insulating layers.

10. The device of claim 9, wherein each of said insulating layers is formed of ceramic material.

11. The device of claim , wherein said ultrasonic vibration generating means and said probe means respectively define internal channels cooperatively coupled together to form a common channel, and further comprising means coupling said common channel to a suction unit; and
   said common channel is branched substantially at its midpoint into a branch channel, said branch channel extending from a rear portion of said casing means in an axial direction of said probe means, and defining an opening for inserting a treatment tool therein.

12. The device of claim 11, wherein said branch channel comprises a valve coupled thereto.

13. The device of claim 12, further comprising a rotary member at least partly defining said channels, and being rotatable about said casing means.

* * * * *